United States Patent
Tzeng et al.

(10) Patent No.: US 10,429,308 B2
(45) Date of Patent: Oct. 1, 2019

(54) CARRIER FOR RAMAN SPECTROSCOPY AND METHOD OF MANUFACTURING THE SAME

(71) Applicant: National Cheng Kung University, Tainan (TW)

(72) Inventors: Yon-Hua Tzeng, Tainan (TW); Ying-Ren Chen, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 0 days.

(21) Appl. No.: 15/815,811

(22) Filed: Nov. 17, 2017

(65) Prior Publication Data
US 2019/0025217 A1  Jan. 24, 2019

(30) Foreign Application Priority Data
Jul. 24, 2017 (TW) .............................. 106124797 A

(51) Int. Cl.
| | | |
|---|---|---|
| G01J 3/44 | (2006.01) |
| G01N 21/65 | (2006.01) |
| C23C 16/511 | (2006.01) |
| C23C 16/02 | (2006.01) |
| C23C 16/26 | (2006.01) |

(52) U.S. Cl.
CPC ....... *G01N 21/658* (2013.01); *C23C 16/0218* (2013.01); *C23C 16/26* (2013.01); *C23C 16/511* (2013.01)

(58) Field of Classification Search
CPC ......... H01L 29/78696; H01L 29/78684; H01L 29/1606; H01L 29/247; H01L 29/78681; H01L 21/02527; H01L 21/02565; G03F 7/16; C23C 16/44; C23C 16/26; C23C 16/08; G23C 16/08
USPC ........................................ 356/301, 319, 326
See application file for complete search history.

(56) References Cited

U.S. PATENT DOCUMENTS

| | | | |
|---|---|---|---|
| 9,105,793 B2* | 8/2015 | Bouchiat | G01N 27/4146 |
| 10,079,313 B2* | 9/2018 | Lee | H01L 29/78696 |
| 2012/0058350 A1* | 3/2012 | Long | B82Y 10/00 428/446 |
| 2015/0198886 A1* | 7/2015 | Lai | H01L 21/02444 428/408 |
| 2016/0284811 A1* | 9/2016 | Yu | H01L 29/454 |

* cited by examiner

*Primary Examiner* — Hoa Q Pham
(74) *Attorney, Agent, or Firm* — Bacon & Thomas, PLLC

(57) ABSTRACT

A carrier for Raman spectroscopy comprising: a substrate having a first metal surface; a plurality of graphene islands disposed on the substrate, wherein parts of the neighboring graphene islands are not connected and thereby form a plurality of gaps between the graphene islands; and a plurality of second metal particles disposed at the gaps between the graphene islands.

22 Claims, 9 Drawing Sheets

CARRIER FOR RAMAN SPECTROSCOPY AND METHOD OF MANUFACTURING THE SAME

CROSS REFERENCE TO RELATED APPLICATION

This application claims the benefits of the Taiwan Patent Application Serial Number 106124797, filed on Jul. 24, 2017, the subject matter of which is incorporated herein by reference.

BACKGROUND OF THE INVENTION

1. Field of the Invention

The present invention relates to a carrier for spectroscopy and method of manufacturing the same and, more particularly, to a carrier for Raman spectroscopy.

2. Description of Related Art

Raman scattering is widely used for detection. When a molecular is excited by a photon to become vibrating or rotating, a portion of the photon energy is absorbed by the molecule leaving the scattered photon with less energy than it originally has. The amount of energy loss by the photon is determined by modes of vibration such as stretching or bending as well as the specific vibration energy. Because molecules of different structures and compositions exhibit different modes and energy of vibration, spectra representing energy of scattered photons after the incident photons of the same original energy have suffered from different amounts of energy losses can be used to distinguish a specific molecule from others. The energy losses are usually presented as a series of increased wavelengths from the original wavelength of incident photons. For convenience, changes in wavenumber instead of wavelength are shown as Raman shift. The aforementioned process results in scattered light with frequency different from the incident light. The frequency variation corresponding to the change of vibration energy is "Raman scattering", and the spectrum of the scattered light presented as the changes in wavenumbers between the incident light and scattered light is "Raman spectrum". Moreover, the difference in frequency, wavelength, or wavenumber between incident light and scattered light is "Raman shift".

Since Ramen shift corresponds to the increase in rotational or vibrational energy of a molecule rather than the frequency of the exciting light, the Raman shift features of different molecules or structures can be applied for detection, identification, and quantification of molecular structures.

Surface enhanced Raman scattering (SERS) is known as one of the most sensitive modern Raman spectroscopy techniques. The principle of SERS can be briefly explained by the following example. When two or more inert metal nanoparticles are close to each other and exposed to appropriate light, the electromagnetic fields of the incident light cause free electrons in metal nanoparticles to move in a direction opposite to the local electric field resulting in separate accumulation of positive and negative charges on opposite sides of a metal nanoparticles and on the neighboring sides of two near-by metal nanoparticles. High density charges of opposite signs at a short distance from each other induce much stronger local electric fields than that of the incident light. Since electric field has positive correlation with the intensity of Raman scattering signal strength, the greater the strength of electric field generated from metal nanoparticles surface and adjacent particles, the greater the intensity of Raman signal is. Thereby, it can enhance detection sensitivity of Raman spectrum so as to make it a potential technology that can be used to detect various trace amount of a molecule in a short period of time. Also it can be widely applied in various technical fields such as biomolecule detection, drug testing, medical diagnosis, and analysis. In addition, as graphene film has excellent optical, electrical, and mechanical properties, it can be used to further improve Raman scattering spectroscopy, too.

In order to make SERS a useful sensor for real-life applications, more affordable and sensitive SERS substrates are desired. If a SERS substrate is made flexible, it can further extend the range of applicability of the excellent SERS molecular sensor. Therefore, less expensive processes than those commonly used for the fabrication of modern integrated circuit are widely sought after for the fabrication of properly located metal nanoparticles of desired sizes, shapes, and plasmonic properties for SERS applications.

SUMMARY OF THE INVENTION

In order to fulfil the aforementioned desires, the present invention provides a carrier for Raman spectroscopy so as to save manufacturing costs of the carrier, to save the manufacturing time, and to manufacture a flexible carrier for Raman spectroscopy.

To achieve the aforementioned object, the present invention provides a carrier for Raman spectroscopy comprising: a substrate having a first metal surface; a plurality of graphene islands disposed on the substrate, wherein parts of the neighboring graphene islands are not connected and thereby form a plurality of gaps between the graphene islands; and a plurality of second metal particles disposed at the gaps between the graphene islands.

According to one preferred embodiment, the graphene islands of the carrier for Raman spectroscopy are graphene nano-islands, and the second metal particles are silver or gold nanoparticles.

In one aspect of the present invention, the carrier for Raman spectroscopy may, by way of example and not limitation, be a copper substrate, a nickel substrate, a platinum substrate, a palladium substrate, a ruthenium substrate, an iridium substrate, a cobalt substrate, an alloy substrate, a quartz substrate comprising the first metal surface, a glass substrate comprising the first metal surface, a third metal substrate comprising the first metal surface, a silicon substrate comprising the first metal surface, or a silicon dioxide substrate comprising the first metal surface.

In one aspect of the present invention, the carrier for Raman spectroscopy may, by way of example and not limitation, be copper, nickel, platinum, palladium, ruthenium, iridium, or cobalt.

In one aspect of the present invention, the third metal may, by way of example and not limitation, be nickel, platinum, palladium, ruthenium, iridium, iron, cobalt, zinc, tin, lead, palladium, titanium, or alloys thereof.

In one aspect of the present invention, the graphene islands can be fabricated on substrate comprising the first metal and then transferred on to a different substrate surface comprising the first metal surface. By transferring graphene islands, the substrate on which graphene islands are transferred onto does not need to withstand the high-temperature process for fabricating graphene islands. The substrate comprising the first metal for the transfer of graphene islands can be for example, but not limited to plastic, paper, aluminum, or wood.

In one aspect of the present invention, the gaps between the graphene islands of the carrier for Raman spectroscopy preferably are in a range of 3 nm-200 nm, more preferably 3 nm-100 nm, and most preferably 3 nm-50 nm.

In one aspect of the present invention, the second metal of the carrier for Raman spectroscopy may, by way of example and not limitation, be gold, silver, or a metal with higher chemical inertness than the first metal.

The present invention further provides a method of manufacturing a carrier for Raman spectroscopy, comprising steps of: (1-A) providing a substrate having a first metal surface; (1-B) forming a plurality of graphene islands on the substrate, wherein parts of the neighboring graphene islands are not connected and thereby form a plurality of gaps between the graphene islands; and (1-C) forming a plurality of second metal particles at the gaps between the graphene islands.

The present invention further provides a method of manufacturing a carrier for Raman spectroscopy, comprising steps of: (2-A) providing a substrate having a first metal surface; (2-B) forming a plurality of graphene islands on the substrate, wherein parts of the neighboring graphene islands are not connected and thereby form a plurality of gaps between the graphene islands; (2-C) transferring the graphene islands on to a second substrate having the first metal surface; and (2-D) forming a plurality of second metal particles at the gaps between the graphene islands.

In one aspect of the present invention, the second substrate may, by way of example and not limitation, be plastic, paper, aluminum, |glass|[劉學模1], ], or wood.

According to one exemplary preferred embodiment of the method of manufacturing the carrier for Raman spectroscopy, the graphene islands are graphene nano-islands, and the second metal particles are silver nanoparticles or gold nanoparticles.

According to one aspect of the method of manufacturing the carrier for Raman spectroscopy, the substrate in the step (1-A) or (2-A) may, by way of example and not limitation, be a copper substrate, a nickel substrate, a platinum substrate, a palladium substrate, a ruthenium substrate, an iridium substrate, a cobalt substrate, an alloy substrate, a quartz substrate comprising the first metal surface, a glass substrate comprising the first metal surface, a third metal substrate comprising the first metal surface, a silicon substrate comprising the first metal surface, or a silicon dioxide substrate comprising the first metal surface.

According to one aspect of the method of manufacturing the carrier for Raman spectroscopy, the first metal in the step (1-A) or (2-A) may, by way of example and not limitation, be copper, nickel, platinum, palladium, ruthenium, iridium, or cobalt.

According to the method of manufacturing the carrier for Raman spectroscopy, the plurality of graphene islands in the step (1-B) or (2-B) are formed by thermal chemical vapor deposition or microwave plasma enhanced chemical vapor deposition.

According to another aspect of the method of manufacturing the carrier for Raman spectroscopy, the step (1-B) or (2-B) comprises forming the plurality of graphene islands on a substrate having the first metal surface by thermal chemical vapor deposition or microwave plasma enhanced chemical vapor deposition. Moreover, the step (2-C) of transferring to another substrate having the first metal surface may be optionally achieved after step (1-B) is performed.

Said another substrate having the first metal surface may be a plastic substrate having the first metal surface or a glass substrate having the first metal surface regardless a high temperature processing limitation of thermal chemical vapor deposition or microwave plasma enhanced chemical vapor deposition.

In further aspect of the method of manufacturing the carrier for Raman spectroscopy, the plurality of graphene islands in the step (1-B) or (2-B) preferably formed by thermal chemical vapor deposition or microwave plasma enhanced chemical vapor deposition.

In yet aspect of the method of manufacturing the carrier for Raman spectroscopy, the plurality of graphene islands in the step (1-B) or (2-B) are more preferably formed by thermal chemical vapor deposition, and precursor gases of the thermal chemical deposition are, by way of example and not limitation, hydrogen and methane.

In further aspect of the method of manufacturing the carrier for Raman spectroscopy, in the step (1-B) or (2-B), a flow rate ratio of hydrogen/methane preferably is 0.5-10: 2-20 sccm, more preferably 4:4 sccm, 4:12 sccm, or 3:15 sccm; and the temperature is in a range of 400° C.-1040° C. and preferably is in a range of 800° C.-1040° C.

In one aspect of the method of manufacturing the carrier for Raman spectroscopy, the hydrogen may, without limitation, react with the methane for 30 seconds to 3 minutes in the step (1-B) or (2-B).

In one aspect of the method of manufacturing the carrier for Raman spectroscopy, the gaps between the graphene islands in the step (1-B) or (2-B) preferably are in a range of 3 nm to 200 nm, more preferably 3 nm to 100 nm, and most preferably 3 nm to 80 nm.

In one aspect of the method of manufacturing the carrier for Raman spectroscopy, the second metal in the step (1-C) or (2-D) may, by way of example and not limitation, be platinum or gold or silver.

In one aspect of the method of manufacturing the carrier for Raman spectroscopy, the second metal particles in the step (1-C) or (2-D) are formed by selective deposition with a solution comprising the second metal; wherein the solution comprising the second metal preferably is silver nitrate or chlorauric acid.

In one aspect of the method of manufacturing the carrier for Raman spectroscopy, the solution comprising the second metal in the step (1-C) or (2-D) preferably is 1 mM to 10 mM silver nitrate of solution or 0.5 mM to 10 mM chloroauric acid solution; more preferably, 5 mM silver nitrate solution or 1 mM chloroauric acid solution.

In one aspect of the method of manufacturing the carrier for Raman spectroscopy, a reaction time in the step (1-C) or (2-D) preferably is in a range of 10 seconds to 150 seconds.

Other objects, advantages, and novel features of the invention will become more apparent from the following detailed description when taken in conjunction with the accompanying drawings.

DETAILED DESCRIPTION OF THE PREFERRED EMBODIMENT

Pre-Preparation Example 1

A copper foil (purity 99.8%, thickness 0.025 mm, size 2 cm×4 cm) was provided, sequentially pre-cleaned by acetone isopropyl alcohol via ultra-sonication for 10 minutes to remove the particles and organic substances, heated in 80° C. of acetic acid for 30 minutes to remove copper oxide on the surface, dried by nitrogen gun, and then heated to 300° C. in atmosphere. Thereafter, a pretreatment of oxidation for the copper foil was carried for 15 minutes, and the copper foil was folded with 2 mm gap.

Preparation Example 1

A chamber comprising a quartz boat in which a copper foil was placed was evacuated to $10^{-6}$ Torr with a turbo-pump and mechanical pump to remove impurities. Afterwards, the evacuation system was switched to mechanical pump. Thereafter, the chamber was filled with $H_2$ flow at 100 sccm and argon flow at 1000 sccm, and then gradually heated at a high temperature region to 1040° C. from room temperature in 50 minutes. The temperature of the high temperature region was maintained at 1040° C. for 10 minutes, followed by annealing for 30 minutes.

After annealing, the Ar flow was turned off, and then methane ($CH_4$) gas flowed into the chamber at 0.2 sccm. After 30 minutes of required processing time, the copper foil was moved out of the high temperature region using a magnetically controlled robot arm. Thereafter, the chamber was filled with Ar flow at 10 sccm for cooling while the heater was turned off. After the temperature of copper foil was cooled back to near room temperature, the copper foil was removed from the chamber and then Sample 1 was obtained.

Preparation Example 2

A chamber comprising a quartz boat where a copper foil was placed was evacuated to $10^{-6}$ Torr with a turbo-pump and mechanical pump to remove impurities. Afterwards, the evacuation system was switched to mechanical pump. Furthermore, the chamber was filled with $H_2$ flow at 15 sccm and Ar flow at 1000 sccm, and then gradually heated at a high temperature region to 1040° C. from room temperature in 50 minutes. The temperature of high temperature region was maintained at 1040° C. for 10 minutes, followed by annealing for 1 hour.

Figure 1A:
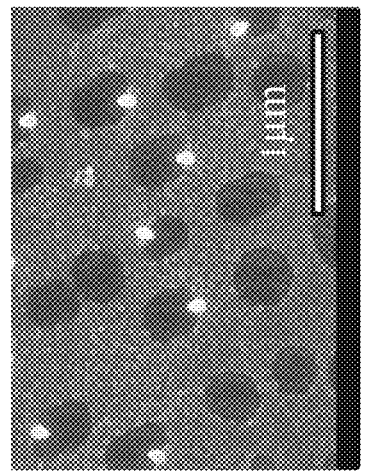
FIG. 1A to FIG. 1F are scanning electron microscopy (SEM) images of graphene nano-islands according to Preparation Example 2 to 4.
Figure 1B:
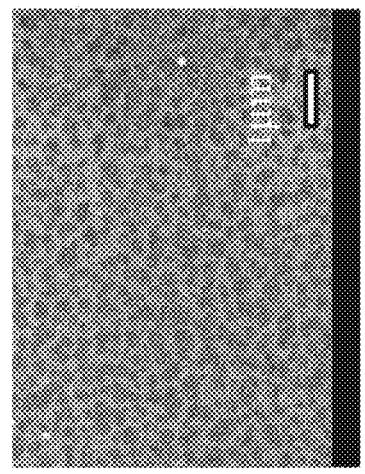

After annealing, the copper foil was allowed to cool down while Ar flow was turned off, and then the chamber was filled with H2 flow at 4 sccm and methane (CH4) flow at 4 sccm for 3 minutes to grow graphene nano-islands (GNIs) on the copper foil. Thereby, Sample 2 was obtained. The size of obtained graphene quantum dots were in a range of 200-300 nm and the number density is 5 dots/μm2 as shown in FIG. 1A. Then the obtained quantum dots were transferred to a SiO2/Si substrate (thickness 300 nm) as shown in FIG. 1B. Afterwards, a Raman scattering spectroscopy was measured to examine the presence of characteristic peaks of graphene. The presence of the D-band near 1350 cm-1, G-band near 1580 cm-1 and 2D band near 2700 cm-1 indicated a graphene layer was on the substrate (not shown).

Preparation Example 3

A chamber comprising a quartz boat in which a copper foil was placed was evacuated to $10^{-6}$ Torr with a turbo-pump and mechanical pump to remove impurities. Afterwards, the evacuation system was switched to mechanical pump. Further, the chamber was filled with $H_2$ flow at 15 sccm and Ar flow at 1000 sccm, and then gradually heated at a high temperature region to 1040° C. from room temperature in 50 minutes. The temperature of high temperature region was maintained at 1040° C. for 10 minutes, followed by annealing for 1 hour.

Figure 1C:
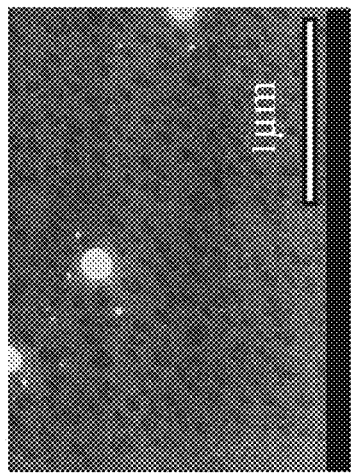
Figure 1D:
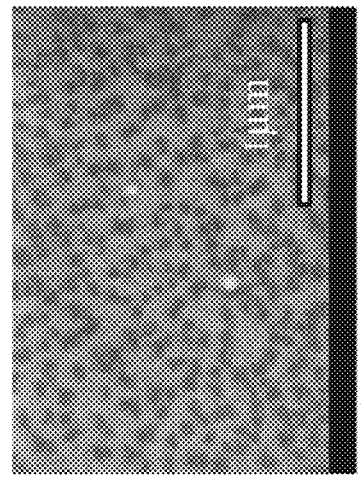

After annealing, the copper foil was allowed to cool down while Ar flow was turned off, and then the chamber was filled with H2 flow at 4 sccm and methane (CH4) flow at 12 sccm for 40 seconds to grow GNIs on the copper foil. Thereby, Sample 3 was obtained. The size of obtained graphene quantum dots were in a range of 40-50 nm and the number density is 70 dots/μm2 as shown in FIG. 1C. Then the obtained quantum dots were transferred to a SiO2/Si substrate (thickness 300 nm) as shown in FIG. 1D. Afterwards, a Raman spectrum measurement was carried out to examine the presence of characteristic peaks of graphene. The presence of the D-band near 1350 cm-1, G-band near 1580 cm-1 and 2D band near 2700 cm-1 indicated a graphene layer was on the substrate (not shown).

Preparation Example 4

A chamber comprising a quartz boat where a copper foil was placed was evacuated to $10^{-6}$ Torr with a turbo-pump and mechanical pump to remove impurities. Afterwards, the evacuation system was switched to mechanical pump. Further, the chamber was filled with $H_2$ flow at 15 sccm and Ar flow at 1000 sccm, and then gradually heated at a high temperature region to 1040° C. from room temperature in 50 minutes. The temperature of high temperature region was maintained at 1040° C. for 10 minutes, followed by annealing for 1 hour.

Figure 1E:
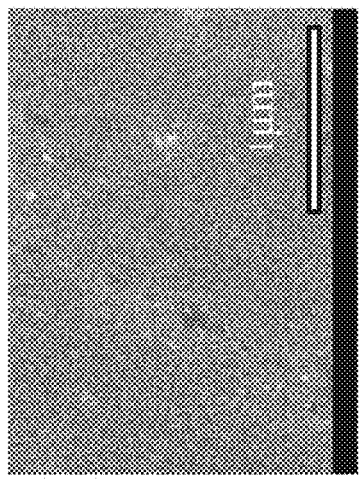
Figure 1F:
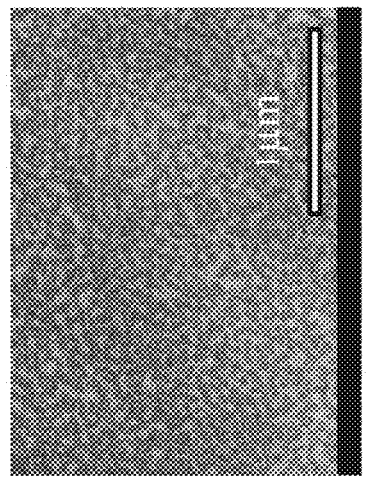

After annealing, the copper foil was allowed to cool down while Ar flow was turned off, and then the chamber was filled with H2 flow at 3 sccm and methane (CH4) flow at 15 sccm for 30 seconds to grow GNIs on the copper foil. Thereby, Sample 4 was obtained. The size of obtained graphene quantum dots were in a range of 20-30 nm and the density that of is 110 dots/μm2 as shown in FIG. 1E. Then the obtained quantum dots were transferred to a SiO2/Si substrate (thickness 300 nm) as shown in FIG. 1F. Afterwards, a Raman spectrum was carried out to examine the presence of characteristic peaks of graphene. The presence of the D-band near 1350 cm-1, G-band near 1580 cm-1 and 2D band near 2700 cm-1 indicated a graphene layer was on the substrate (not shown).

Preparation Example 5

A chamber comprising a quartz boat where a copper foil was placed was evacuated to $10^{-6}$ Torr with a turbo-pump and mechanical pump to remove impurities. Afterwards, the evacuation system was switched to mechanical pump. Further, the chamber was filled with $H_2$ flow at 15 sccm and Ar flow at 1000 sccm, and then gradually heated at a high temperature region to 1040° C. from room temperature in 50 minutes. The temperature of high temperature region was maintained at 1040° C. for 10 minutes, followed by annealing for 1 hour.

Figure 2:
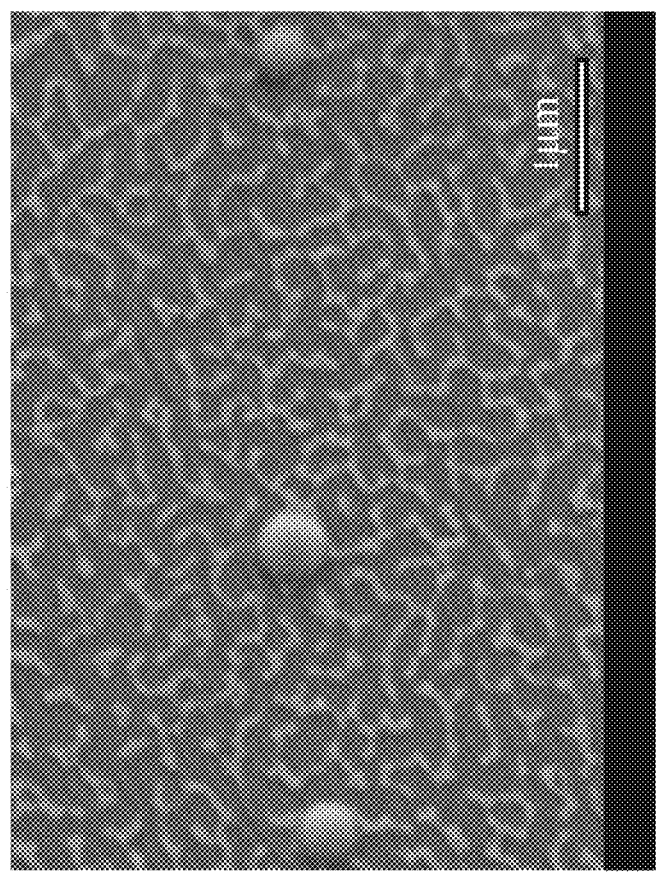
FIG. 2 is a SEM image of graphene nano-islands according to Preparation Example 5.
Figure 3:
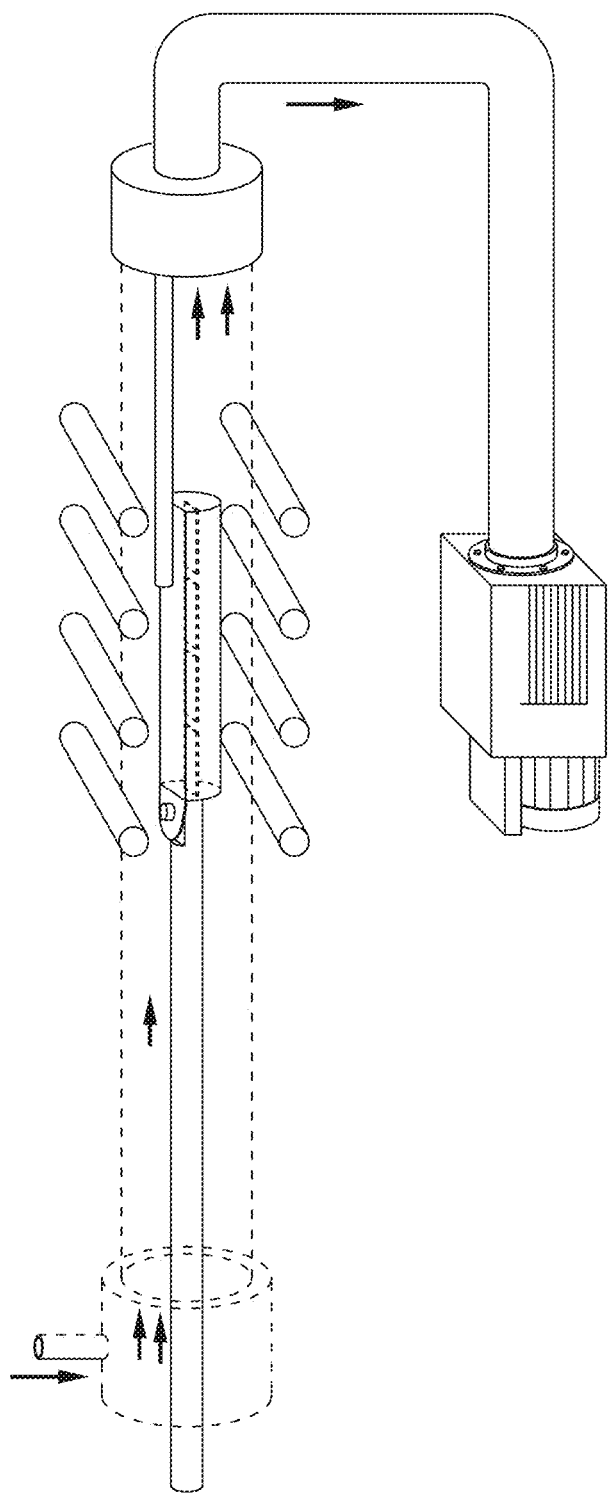
FIG. 3 is a schematic diagram of thermal chemical vapor deposition system according to one preferred embodiment.
Figure 4:
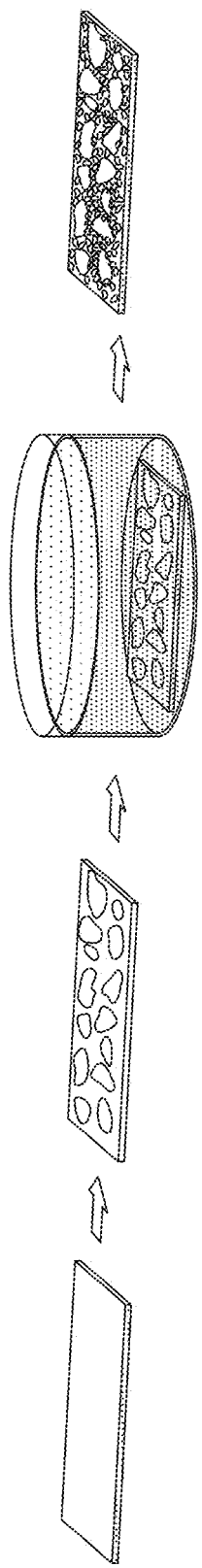
FIG. 4 is a manufacturing process diagram for the formation of graphene/Ag nanoparticles composite substrate according to one preferred embodiment.

After annealing, the copper foil was allowed to cool down while Ar flow was turned off, and then the chamber was filled with $H_2$ flow at 4 sccm and $CH_4$ flow at 12 sccm for 2 minutes to grow GNIs on the copper foil. Thereby, Sample 5 was obtained. Further, gaps between obtained GNIs were about in a range of 30-50 nm, as shown in FIG. 2. Then the obtained GNIs were transferred to a $SiO_2$/Si substrate (thickness 300 nm; not shown). Afterwards, a Raman spectrum was carried out to examine the presence of characteristic peaks of graphene. The presence of the D-band near 1350 $cm^{-1}$, G-band near 1580 $cm^{-1}$ and 2D band near 2700 cm' indicated a graphene layer was on the substrate (not shown).

Preparation Example 6

Figures 5A, 5B:
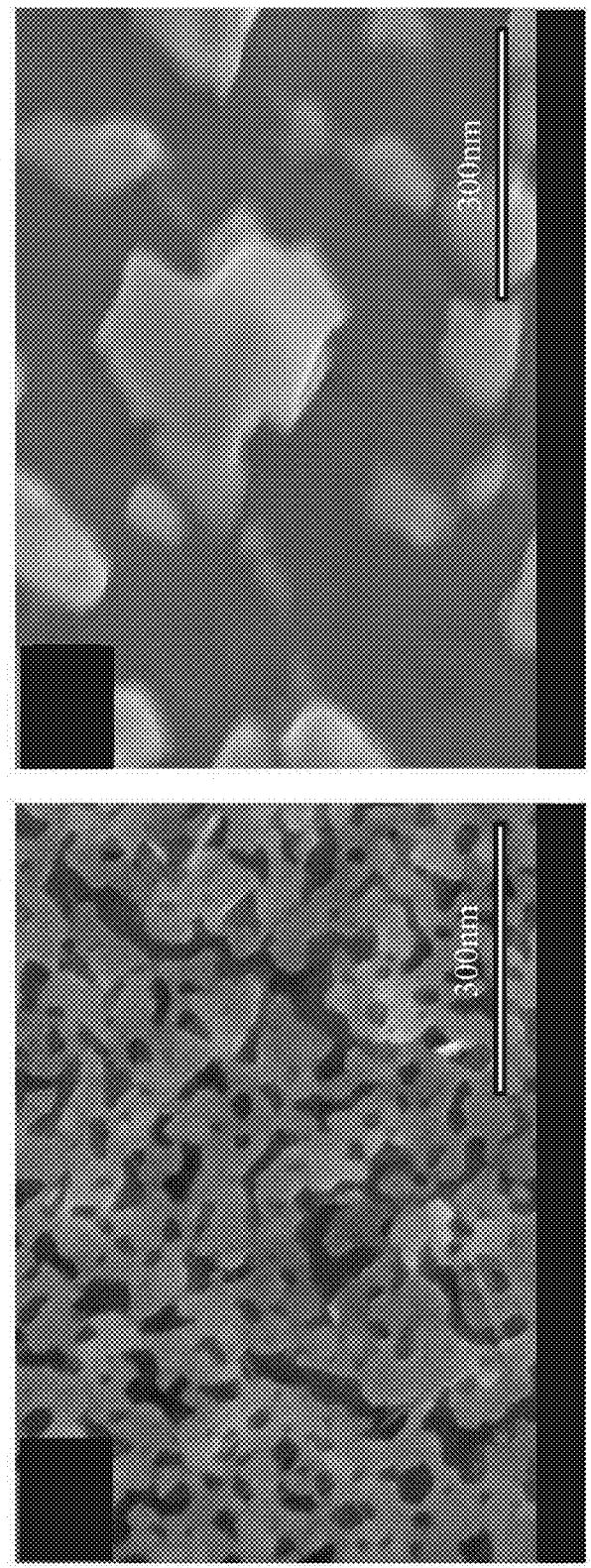
FIG. 5A and FIG. 5B are SEM images of different silver morphologies according to Preparation Example 6 and 7.

A Sample 3 from Preparation Example 3 was provided and immersed in 5 mM silver nitrate (AgNO3) aqueous solution at a condition of 1 atm and room temperature (27° C.) for 2 minutes to carry out silver mirror reaction to form two-dimensional silver particle arrays surrounding and embedded along edges of graphene. As shown in FIG. 5A, the two-dimensional silver particles have acute angled ends. Hence, a combination of two-dimensional silver particle array and Sample 3, i.e. the Carrier 1, was obtained.

Preparation Example 6

A Sample 5 from Preparation Example 5 was provided and immersed in 5 mM silver nitrate (AgNO3) aqueous solution at a condition of 1 atm and room temperature (27° C.) for 2 minutes to carry out silver mirror reaction to form one-dimensional silver particle arrays surrounding and embedded along edges of graphene. As shown in FIG. 5B, the one-dimensional silver particles have acute angled ends. Hence, a combination of one-dimensional silver particle arrays and Sample 5, i.e. the Carrier 2, was obtained.

Test Example 1

In the present test example, various concentration of R6G molecule was used to examine whether the formation of silver nanoparticles (AgNPs) between graphene can remarkably enhance Raman signal.

A Carrier 2, a Sample 5, a copper foil with graphene film on the surface, and a copper foil were respectively immersed in R6G solution ($10^{-5}$M) for 5 minutes, washed by deionized water three times, dried with a nitrogen gun, and then detected characteristic Raman signal of R6G through 532 nm green laser.

A Carrier 2, a Sample 5, a copper foil with graphene film on the surface, and a copper foil were respectively immersed in R6G solution ($10^{-8}$M) for 5 minutes, washed by deionized water three times, dried with a nitrogen gun, and then detected characteristic Raman signal of R6G through 532 nm green laser.

Figures 6A, 6B:
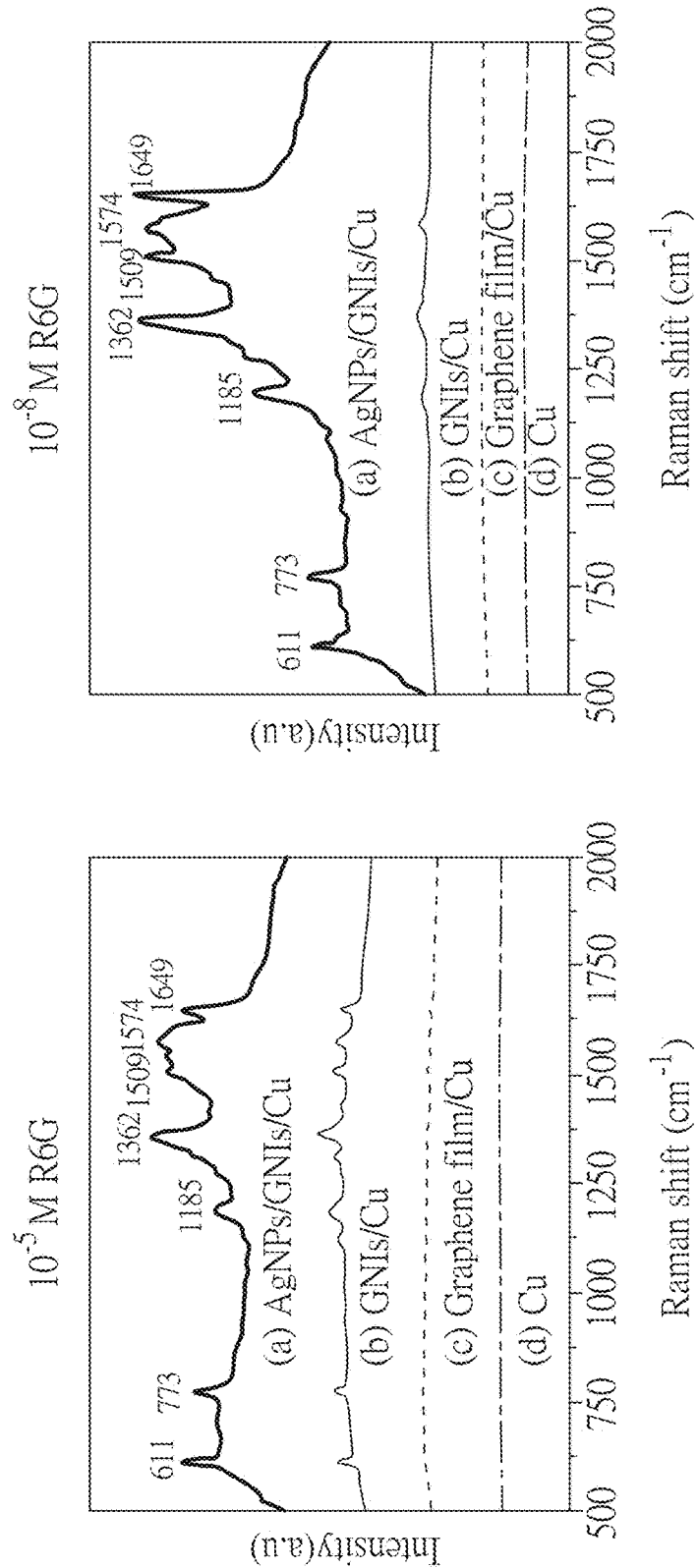
FIG. 6A and FIG. 6B are graphs which show one-dimensional Ag nanoparticles (AgNPs) surrounding and embedded along graphene nano-islands (GNIs) can enhance detection capability for R6G molecules.

As shown in FIG. 6A, the copper foil with graphene film on the surface could not indicate characteristic peaks of 10-5M R6G. Furthermore, a detection limitation of Sample 5 is 10-8M, whereas Carrier 2 still exhibited excellent detection ability to 10-8M R6G.

Test Example 2

In the present test example, $9\times10^{-12}$M R6G molecule was used to examine the ability of two-dimensional silver particle arrays to enhance Raman signal under different reaction time of silver mirror reaction.

Figure 7:
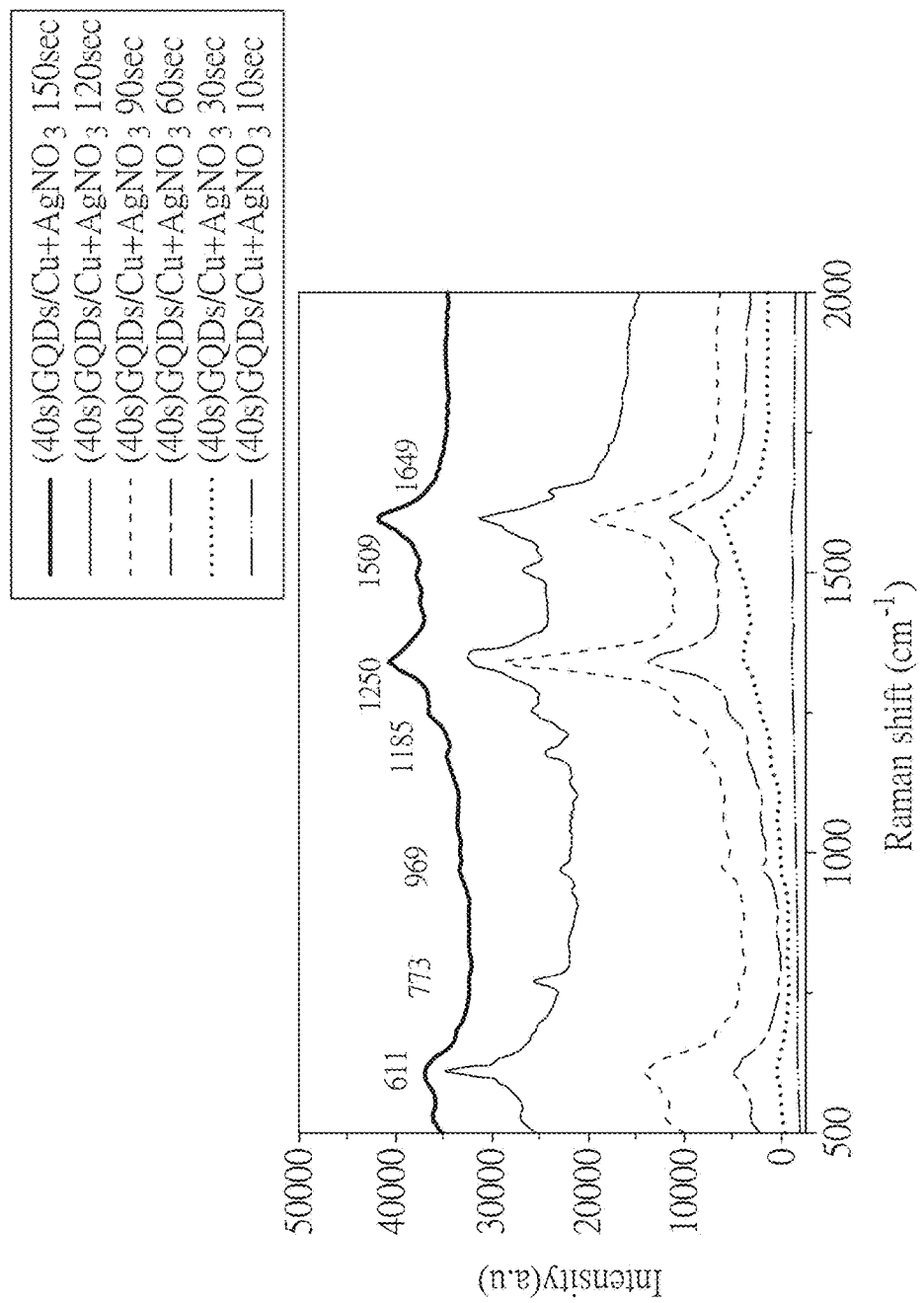
FIG. 7 is a Raman signal graph that shows enhancement of detection ability for R6G molecules ($9\times10^{-12}$M) under different reaction time of plating silver.

A Sample 3 from Preparation Example 3 was provided and immersed in 5 mM silver nitrate (AgNO3) aqueous solution at a condition of 1 atm and room temperature (27° C.) for 10, 30, 60, 90, 120, or 150 seconds to carry out silver mirror reaction to form a two-dimensional silver particle arrays surrounding and embedded along edges of graphene. Said Sample 3 with different reaction time of silver mirror reaction were immersed in R6G solution ($9\times10^{-12}$M), washed by deionized water three times, dried with a nitrogen gun, and then detected characteristic Raman signal of R6G through 532 nm green laser as shown in FIG. 7. It was found that Sample 3 with 120 seconds of reaction time of silver mirror reaction enhanced Raman signal most. The expected results demonstrated that adequate gap between particles could lead to an enhancement of physical mechanism of intense electromagnetic field. Furthermore, the gaps between nanoparticles were about 3-10 nm, and the nanoparticles surrounding graphene could bring effective fluorescence quenching as to raise signal-to-noise ratio, namely reduce the impact of fluorescence background (enhancement of chemical mechanism) on Raman spectrum.

Test Example 3

In the present test example, different concentration of R6G ($9\times10^{-10}$M-$9\times10^{-16}$M) were used to examine the detection capability of two-dimensional silver particle arrays surrounding and embedded along graphene quantum dots.

A plurality of Carrier 1 was respectively immersed in different concentration of R6G solution ($9\times10^{-10}$M-$9\times10^{-16}$M) for 5 minutes, washed by deionized water three times, dried with a nitrogen gun, and then detected characteristic Raman signal of R6G through 532 nm green laser.

Figure 8:
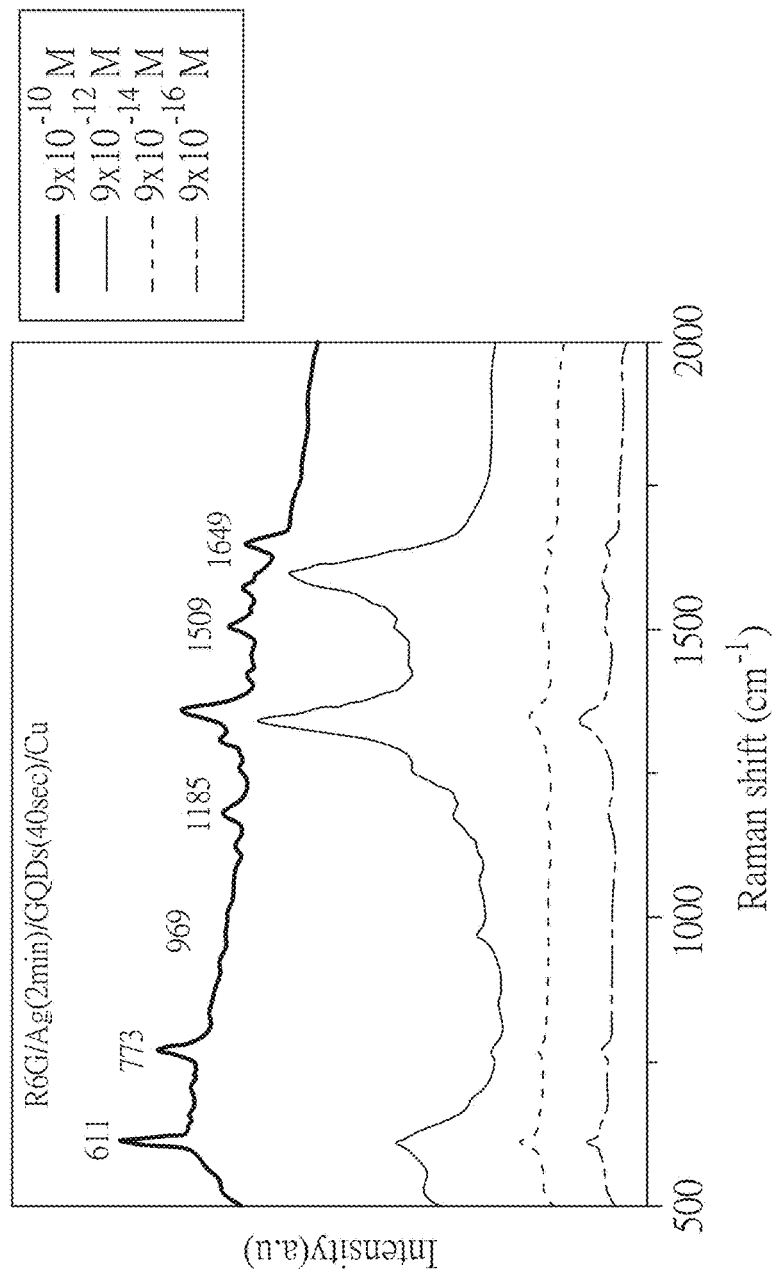
FIG. 8 is a Raman signal graph that shows detection ability of two-dimensional Ag particles arrays for different concentration of R6G molecules.

As shown in FIG. 8, for the detection of R6G molecules, the enhancement factor for Raman scattering signal strength by the SERS sensor was as high as $10^{14}$ times according to enhanced Raman scattering signal strength in relation to R6G concentration. This is because gaps of two-dimensional Ag nanoparticles enhance local electromagnetic field and fluorescence quenching ability of graphene quantum dots.

Test Example 4

A plurality of Sample 3 from Preparation Example 3 were respectively immersed in 1 mM chloroauric acid ($HAuCl_4$) solution for 10, 30, 60, 90, 120, or 150 seconds to form two-dimensional Au particles array surrounding and embedded along the edge of graphene.

Figure 9:
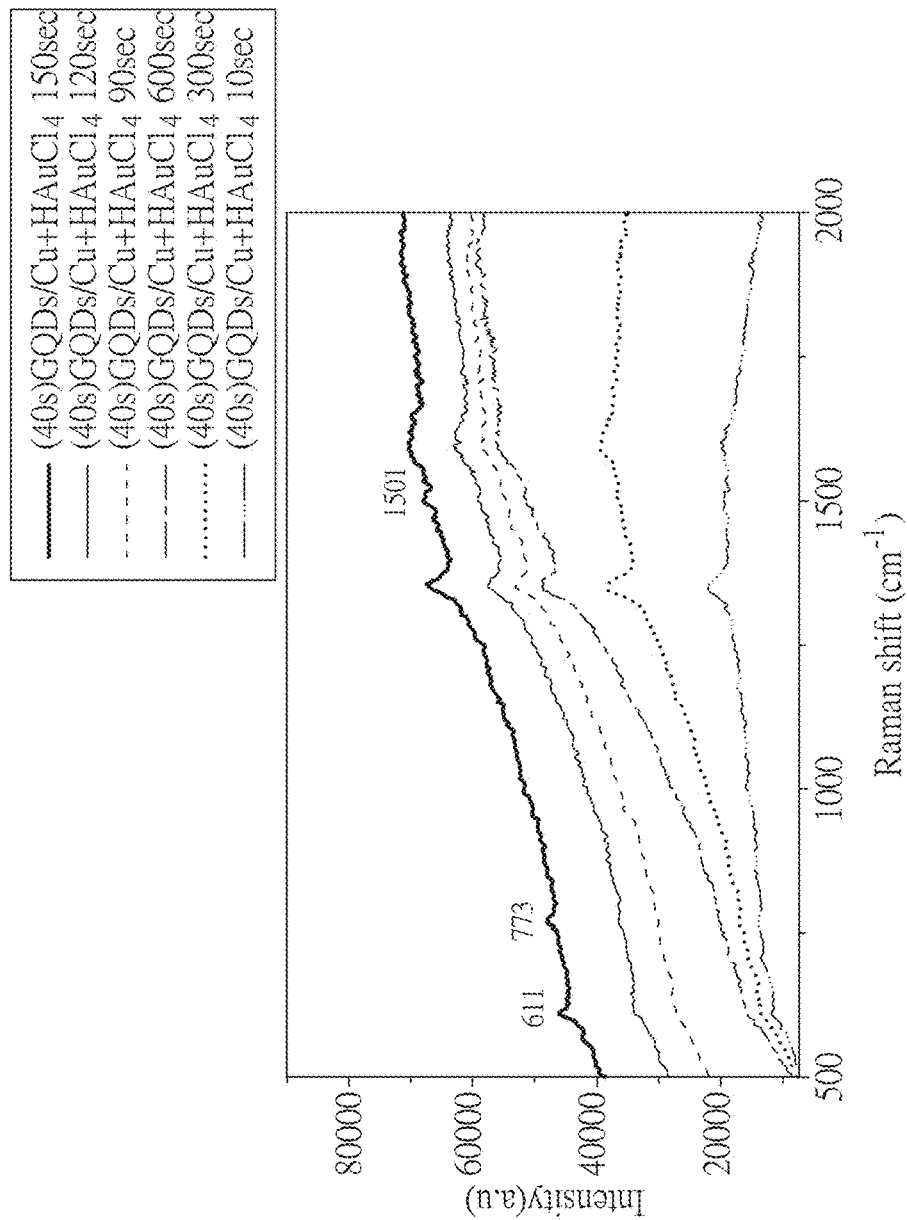
FIG. 9 is a Raman signal graph that shows enhancement of detection ability for R6G molecules ($9\times10^{-12}$M) under different reaction time of plating gold.

As shown in FIG. 9, R6G molecule ($9\times10^{-12}$M) was used to examine the detection capability of two-dimensional Au particle arrays surrounding and embedded along graphene quantum dots. Signal was found in Sample 3 with 150 seconds of the reaction time. The present invention successfully overcomes difficulties in manufacturing traditional graphene/silver composite substrate for surface-enhanced Raman scattering. In addition, the present invention provides a rapid way to fabricate graphene patterns through thermal chemical vapor deposition, form metal nanoparticles (such as Au and Ag) at nano-scaled gaps through selective deposition, and thereby to form one- or two-dimensional metal nano-arrays. Metal coating and formation of graphene patterns by expensive semiconductor processes may be exempted from the manufacturing method provided herein. Therefore, SERS chips provided by the present invention can be mass produced, and have advantages such as flexibility, high sensitivity, high reliability, and high detection capability. Further, graphene exhibits a multiple function in the present invention, for example, forming adequate distance (3-10 nm) between metal nanoparticles; fluorescence quenching (chemical mechanism); π-π* attraction to plane molecule; and protection for copper substrate against redox reactions. The self-patterned graphene shows excellent detection ability by introducing self-assembled metal nanoparticles (electromagnetic field mechanism) and fluorescence quenching capability of graphene.

Although the present invention has been explained in relation to its preferred embodiment, it is to be understood that many other possible modifications and variations can be made without departing from the spirit and scope of the invention as hereinafter claimed.

What is claimed is:

1. A carrier for Raman spectroscopy comprising:
    a substrate having a first metal surface;
    a plurality of graphene islands disposed on the substrate, wherein parts of the neighboring graphene islands are not connected and thereby form a plurality of gaps between the graphene islands; and
    a plurality of second metal particles disposed at the gaps between the graphene islands.

2. The carrier according to claim 1, wherein the graphene islands are graphene nano-islands, and the second metal particles are silver nanoparticles or gold nanoparticles.

3. The carrier according to claim 1, wherein the carrier is a copper substrate, a nickel substrate, a platinum substrate, a palladium substrate, a ruthenium substrate, an iridium substrate, a cobalt substrate, an alloy substrate, a quartz substrate comprising the first metal surface, a glass substrate comprising the first metal surface, a third metal substrate comprising the first metal surface, a silicon substrate comprising the first metal surface, or a silicon dioxide substrate comprising the first metal surface.

4. The carrier according to claim 1, wherein the first metal is copper, nickel, platinum, palladium, ruthenium, iridium, or cobalt.

5. The carrier according to claim 1, wherein the gaps between the graphene islands are in a range of 3 nm to 200 nm.

6. The carrier according to claim 1, wherein the second metal is gold, silver, or a metal with higher chemical inertness than the first metal.

7. A method of manufacturing a carrier for Raman spectroscopy, comprising steps of:
    (1-A) providing a substrate having a first metal surface;
    (1-B) forming a plurality of graphene islands on the substrate, wherein parts of the neighboring graphene islands are not connected and thereby form a plurality of gaps between the graphene islands; and
    (1-C) forming a plurality of second metal particles at the gaps between the graphene islands.

8. The method according to claim 7, wherein the graphene islands are graphene nano-islands, and the second metal particles are silver nanoparticles or gold nanoparticles.

9. The method according to claim 7, wherein the substrate in the step (1-A) is a copper substrate, a nickel substrate, a platinum substrate, a palladium substrate, a ruthenium substrate, an iridium substrate, a cobalt substrate, an alloy substrate, a quartz substrate comprising the first metal surface, a glass substrate comprising the first metal surface, a third metal substrate comprising the first metal surface, a silicon substrate comprising the first metal surface, or a silicon dioxide substrate comprising the first metal surface.

10. The method according to claim 7, wherein the first metal in the step (1-A) is copper, nickel, platinum, palladium, ruthenium, iridium, or cobalt.

11. The method according to claim 7, wherein the plurality of graphene islands in the step (1-B) are formed by thermal chemical vapor deposition or microwave plasma enhanced chemical vapor deposition.

12. The method according to claim 11, wherein the plurality of graphene islands in the step (1-B) are formed by thermal chemical deposition, and precursor gases of the thermal chemical deposition are hydrogen and methane.

13. The method according to claim 12, wherein a flow rate ratio of hydrogen/methane is 0.5-10:2-20 sccm and the temperature is in a range of 800° C.'-1040° C. in the step (1-B).

14. The method according to claim 13, wherein the hydrogen reacts with the methane for 30 seconds to 3 minutes in the step (1-B).

15. The method according to claim 7, wherein the gaps between the graphene islands are in a range of 3 nm to 200 nm.

16. The method according to claim 7, wherein the second metal in the step (1-C) is gold, silver, or a metal with higher chemical inertness than the first metal.

17. The method according to claim 7, wherein the second metal particles in the step (1-C) are formed by selective deposition with a solution comprising the second metal.

18. The method according to claim 17, wherein the solution comprising the second metal in the step (1-C) is a silver nitrate or chloroauric acid solution.

19. The method according to claim 18, wherein the solution comprising the second metal in the step (1-C) is in a range of 1 mM to 10 mM silver nitrate solution or 0.5 mM to 10 mM chloroauric acid solution.

20. The method according to claim 18, wherein a reaction time in the step (1-C) is in a range of 10 seconds to 150 seconds.

21. The method according to claim 7, wherein the step (1-B) further comprises step (2-C) of transferring the graphene islands on to a second substrate having the first metal surface.

22. The method according to claim 21, the second substrate is plastic, paper, aluminum, glass or wood.

* * * * *